United States Patent
Schilling et al.

(10) Patent No.: US 9,920,348 B2
(45) Date of Patent: Mar. 20, 2018

(54) MICROORGANISM FOR EXPRESSING A HUMAN MEMBRANE PROTEIN

(71) Applicant: Novozymes A/S, Bagsvaerd (DK)

(72) Inventors: Michael Schilling, Berlin (DE); Christine Lang, Berlin (DE); Andreas Raab, Berlin (DE)

(73) Assignee: Novozymes A/S, Bagsvaerd (DK)

( * ) Notice: Subject to any disclaimer, the term of this patent is extended or adjusted under 35 U.S.C. 154(b) by 217 days.

(21) Appl. No.: 14/458,639

(22) Filed: Aug. 13, 2014

(65) Prior Publication Data

US 2015/0093781 A1  Apr. 2, 2015

Related U.S. Application Data

(63) Continuation of application No. 13/321,371, filed as application No. PCT/DE2010/000401 on Apr. 1, 2010, now abandoned.

(51) Int. Cl.
*C12P 33/00* (2006.01)
*C07K 14/705* (2006.01)
*C12P 21/02* (2006.01)
*C12N 15/81* (2006.01)

(52) U.S. Cl.
CPC ............ *C12P 33/00* (2013.01); *C07K 14/705* (2013.01); *C12N 15/81* (2013.01); *C12P 21/02* (2013.01)

(58) Field of Classification Search
None
See application file for complete search history.

(56) References Cited

U.S. PATENT DOCUMENTS 5,759,801 A   6/1998 Chenivesse et al.

FOREIGN PATENT DOCUMENTS

| EP | 0486290 A2 | 5/1992 |
|---|---|---|
| JP | 2004141125 | 5/2004 |
| WO | 03/064650 A1 | 8/2003 |

OTHER PUBLICATIONS

N. Eifler, et al., "Functional expression of mammalian receptors and membrane channels in different cells", Journal of Structural Biology 159 (2007), 179-193.
C. Midgett, et al., "Breaking the bottleneck: Eukaryotic membrane protein expression for high-resolution structural studies", Journal of Structural Biology 160 (2007), 265-274.
O.H. Ollila, et al., "Role of sterol type on lateral pressure profiles of lipid membranes affecting membrane protein functionality: Comparison between cholesterol, desmosterol, 7-dehydrocholesterol and ketosterol", Journal of Structural Biology 159 (2007), 311-323.
C.G. Tate, "Overexpression of mammalian integral membrane proteins for structural studies", FEBS Letters 504 (2001) 94-98.
M. Opekarova, et al., "Specific lipid requirements of membrane proteins—a putative bottleneck in heterologous expression", Biochimica et Biophysica Acta 1610 (2003), 11-22.
C. Tate, et al., "Comparison of seven different heterologous protein expression systems for the production of the serotonin transporter", Biochimica et Biophysica Acta 1610 (2003), 141-153.
S. Wagner, et al., "Rationalizing membrane protein overexpression", Trends in Biotechnology vol. 24 No. 8, 2006.

*Primary Examiner* — Kagnew H Gebreyesus
(74) *Attorney, Agent, or Firm* — Eric J. Fechter (57) ABSTRACT

The invention relates to an isolated, genetically modified, living non-mammal organism, having increased HMG-CoA-reductase activity compared to the wild type, and having reduced C24-methyltransferase and/or delta22-desaturase activity compared to the wild type. The invention is characterized in that the organism has increased dehydrocholesterol-delta70-reductase activity compared to the wild type. The invention further relates to different uses of such an organism, to a test kit comprising such an organism, and to a membrane extract of such an organism.

7 Claims, 3 Drawing Sheets

ATGGACCAATTGGTGAAAACTGAAGTCACCAAG
AAGTCTTTTACTGCTCCTGTACAAAAGGCTTCTACACCAGTTTTAACCAATAAAACAGTC
ATTTCTGGATCGAAAGTCAAAAGTTTATCATCTGCGCAATCGAGCTCATCAGGACCTTCA
TCATCTAGTGAGGAAGATGATTCCCGCGATATTGAAAGCTTGGATAAGAAAATACGTCCT
TTAGAAGAATTAGAAGCATTATTAAGTAGTGGAAATACAAAACAATTGAAGAACAAAGAG
GTCGCTGCCTTGGTTATTCACGGTAAGTTACCTTTGTACGCTTTGGAGAAAAAATTAGGT
GATACTACGAGAGCGGTTGCGGTACGTAGGAAGGCTCTTTCAATTTTGGCAGAAGCTCCT
GTATTAGCATCTGATCGTTTACCATATAAAAATTATGACTACGACCGCGTATTTGGCGCT
TGTTGTGAAAATGTTATAGGTTACATGCCTTTGCCCGTTGGTGTTATAGGCCCCTTGGTT
ATCGATGGTACATCTTATCATATACCAATGGCAACTACAGAGGGTTGTTTGGTAGCTTCT
GCCATGCGTGGCTGTAAGGCAATCAATGCTGGCGGTGGTGCAACAACTGTTTTAACTAAG
GATGGTATGACAAGAGGCCCAGTAGTCCGTTTCCCAACTTTGAAAAGATCTGGTGCCTGT
AAGATATGGTTAGACTCAGAAGAGGGACAAAACGCAATTAAAAAGCTTTTAACTCTACA
TCAAGATTTGCACGTCTGCAACATATTCAAACTTGTCTAGCAGGAGATTTACTCTTCATG
AGATTTAGAACAACTACTGGTGACGCAATGGGTATGAATATGATTTCTAAAGGTGTCGAA
TACTCATTAAAGCAAATGGTAGAAGAGTATGGCTGGGAAGATATGGAGGTTGTCTCCGTT
TCTGGTAACTACTGTACCGACAAAAAACCAGCTGCCATCAACTGGATCGAAGGTCGTGGT
AAGAGTGTCGTCGCAGAAGCTACTATTCCTGGTGATGTTGTCAGAAAAGTGTTAAAAAGT
GATGTTTCCGCATTGGTTGAGTTGAACATTGCTAAGAATTTGGTTGGATCTGCAATGGCT
GGGTCTGTTGGTGGATTTAACGCACATGCAGCTAATTTAGTGACAGCTGTTTTCTTGGCA
TTAGGACAAGATCCTGCACAAAATGTTGAAAGTTCCAACTGTATAACATTGATGAAAGAA
GTGGACGGTGATTTGAGAATTTCCGTATCCATGCCATCCATCGAAGTAGGTACCATCGGT
GGTGGTACTGTTCTAGAACCACAAGGTGCCATGTTGGACTTATTAGGTGTAAGAGGCCCG
CATGCTACCGCTCCTGGTACCAACGCACGTCAATTAGCAAGAATAGTTGCCTGTGCCGTC
TTGGCAGGTGAATTATCCTTATGTGCTGCCCTAGCAGCCGGCCATTTGGTTCAAAGTCAT
ATGACCCACAACAGGAAACCTGCTGAACCAACAAAACCTAACAATTTGGACGCCACTGAT
ATAAATCGTTTGAAAGATGGGTCCGTCACCTGCATTAAATCCTAA

MICROORGANISM FOR EXPRESSING A HUMAN MEMBRANE PROTEIN

CROSS REFERENCE TO RELATED APPLICATIONS

This application is a continuation of Ser. No. 13/321,371, filed Feb. 23, 2012 entitled "MICROORGANISM FOR EXPRESSING A HUMAN MEMBRANE PROTEIN", which is a 371 National Phase of PCT/DE2010/000401, filed Apr. 1, 2010, which claims benefit and priority to German Application No. 10 2009 022 772.5, filed May 21, 2009, all of which are hereby incorporated herein by reference in their entity.

FIELD OF THE INVENTION

The invention relates to an isolated genetically modified living non-mammal organism, having increased HMG-CoA reductase activity compared to the wild type, and having a reduced C24 methyltransferase and/or delta22 desaturase activity compared to the wild type, to the uses thereof, a nucleic acid construct for the production thereof, a kit containing the organism, and a membrane extract of such an organism.

PRIOR ART AND BACKGROUND OF THE INVENTION

An organism of the structure mentioned above is known from the document WO 03/064650. This organism is suitable for the biosynthesis of 7-dehydrocholesterol. The motivation for creating this organism is based on the need to produce precursor products to vitamin D3, in particular 7-dehydrocholesterol, in large amounts and under economical conditions.

In a completely different context, there is a need of membrane proteins, in particular human membrane proteins, functionally in a native conformation in at least analytically well acceptable amounts or to make systems available that contain these proteins in a functionally active manner in an amount being for instance sufficient for screening purposes. In principle, for instance biosynthesis methods by means of microorganisms can be used for this. The heterologous expression of membrane proteins from mammal cells in wild type strains, however, often involves difficulties because of the lack of cholesterol, or the presence of ergosterol, respectively, since the expressed membrane proteins are often functionally limited or inactive. This can be explained by the well known fact that sterols in the membranes play an important role for correct folding and the induction of an active conformation of membrane proteins and thus their functionality, i.e. for a functional expression of heterologous membrane proteins in a yeast, the sterol pattern of the membranes must match the membrane protein.

Sterols are an essential constituent of the membranes of eukaryotic cells. They are responsible for the fluidity and permeability of the membranes. Particularly noteworthy is their contribution to the regulation of numerous membrane proteins. They are important as a kind of cofactors for correct folding, stability and activity of the membrane proteins. Free sterols can be found in eukaryotic cells in the plasma membrane and the membranes of all cells compartments. In the lipid particles, sterols occur in an esterified form as storage lipids. In yeasts, the largest part of the free sterols is located in the plasma membrane, followed by the secretory vesicles, and the amount in microsomes, vacuoles and mitochondrial membranes is small. Ergosterol is the final product of the sterol biosynthesis pathway for instance in the yeast *S. cerevisiae* and is the main sterol in the plasma membrane and the secretory vesicles. The membranes of the subcellular compartments contain smaller amounts of sterols, but also other sterol intermediates.

In mammal cells, the final product of the sterol biosynthesis is cholesterol, which is the largest part of the sterols in the plasma membrane. The plasma membrane contains approx. 60-80% of the total cellular cholesterol, the ER, the place of the sterol synthesis, contains only approx. 0.5-1%.

For instance, in the document Wildt, S., Gerngross, T. U., Nature Reviews (2005)3:119-128, a humanization of yeasts is discussed. The term humanization herein relates, however, to the glycosylation pattern of heterologously produced proteins, which has been adapted to human protein, and not to the sterol pattern being relevant for the present invention. Mainly, the synthesis of enzymes or antibodies is treated, and not the one of membrane proteins.

The ergosterol biosynthesis pathway of yeasts can be subdivided into the pre-squalene pathway, i.e. the synthesis of squalene from acetyl-CoA molecules, and the post-squalene pathway, in which the reaction of squalene to ergosterol is catalyzed. As main pacemaker enzyme of the pre-squalene pathway, the hydroxy-methylglutaryl coenzyme A reductase (HMG-CoA reductase) was identified. The high energy-consuming ergosterol biosynthesis pathway is regulated mainly by this enzyme, which is subject therefore to numerous regulation mechanisms, such as e.g. the feedback inhibition by ergosterol. The pre-squalene and the post-squalene pathway, up to the synthesis of zymosterol, proceed in yeast and mammal cells in the same way. The differences downstream of zymosterol to ergosterol or cholesterol are explained in the following. With yeast cells, zymosterol is reacted by C24 methyltransferase to fecosterol, then by delta7-delta8 isomerase to episterol, by delta5 desaturase to ergosta-5,7,24(28)-trienol, by delta22 desaturase to ergosta-5,7,22,24(28)-tetraenol and finally by delta24 reductase to ergosterol. With mammal cells, zymosterol is reacted by delta7-delta8 isomerase to cholesta-7,24-dienol, by delta5 desaturase to cholesta-5,7,24-trienol and by delta7 reductase to desmosterol, and finally by sterol-delta5 desaturase to cholesterol. The last-mentioned enzyme can also react cholesta-7,24-dienol to lathosterol and cholesta-5,7,24-trienol to 7-dehydrocholesterol. Lathosterol in turn can be reacted by delta5 desaturase to 7-dehydrocholesterol. The latter in turn reacts by delta7 reductase also to cholesterol.

An example for a human membrane protein is the serotonin transporter (SERT). It belongs to the family of the $Na^+/Cl^-$-dependent neurotransmitter transporters, which are responsible for the re-uptake of biogenic amines from the synaptic space back to the presynaptic neurons. Further members of this family are the transporters for noradrenaline, dopamine, choline, glycine and γ-aminobutyric acid. The serotonin transporter has a high clinical importance as a pharmacological target molecule of many antidepressants. The antidepressants, the target of which is the SERT, can be subdivided into two main groups: On the one hand the tricyclic agent molecules, such as e.g. imipramine, desimipramine, clomipramine, and on the other hand the SSRI's (selective serotonin re-uptake inhibitors). To the latter group belong active agents such as e.g. paroxetine, fluoxetine, sertraline and citalopram.

Up to now, the SERT was cloned from the human, rat, mouse, bovine and fruit fly *Drosophila melanogaster* tissue. The SERT was expressed in all common systems, i.e. in *E. coli* and the yeast *Pichia pastoris*, in insect cells and in different cell lines, such as for instance COS-1 cells, BHK cells, Hela cells and HEK cells. An expression of the SERT in the yeast *Saccharomyces cerevisiae* is not known. Up to now, a functional expression could only be achieved in mammal cell lines, and in insect cells, not however in *E. coli* or *Pichia pastoris*. The SERT is an extremely difficult protein with regard to heterologous or overexpression. Difficulties occur mainly by the dependence of the serotonin transporter on cholesterol in the membrane surrounding the protein and the importance of the glycosylation for the correct folding of the protein. An activity of the serotonin transporter can only be detected, when cholesterol is present in the membrane. Presumably, this sterol induces a conformal condition of the SERT, which is optimal for its activity. Up to now, it was assumed that the lack of cholesterol in the membrane cannot be compensated by substitution by other sterols. Because of the importance of the cholesterol for the SERT, it is clear, why a functional expression in *E. coli* has not succeeded up to now. By western blot experiments, Tate et al. (Tate, C. G., Haase, J., Baker, C., Boorsma, M., Magnani, F., Vallis, Y., and Williams, D. C., Biochimica et Biophysica Acta (2003) 1610, 141-153) could show that the rSERT is glycosylated, but not functionally expressed in *Pichia pastoris*. The assumption is obvious that the lack of cholesterol in the yeast is responsible for this.

The documents Xu S H, Nes W D, Biochem Biophys Res Commun (1988)155(1):509-17 and WO-2005/121315 A describe cholesterol-producing yeasts. In a different context, a yeast-based system for use in screening methods is known from the document US-2005/0054108 A1.

A modified organism, for instance a strain of the yeast *Saccharomyces cerevisiae*, which is capable to synthesize cholesterol or a pre-stage, which can compensate the lack of cholesterol with regard to the serotonin transporter, would for the first time give point to making possible a functional expression of this protein in non-mammals. In the case of a functional expression, such an organism could be used as a basis for the design of a "bioassay". With this "bioassay", novel pharmacologically relevant active agents for the serotonin transporter could be identified by the "screening" different substance groups. Furthermore, such a yeast strain could also be used for the functional expression of other cholesterol-dependent membrane proteins. The list of the human membrane proteins, for which a cholesterol dependence was detected or is assumed, is long and grows constantly. The list of the diseases and infections, in the pathogenesis of which cholesterol-dependent proteins are involved, is equally long. A system being suitable as a platform for the expression of these proteins could therefore be extremely valuable.

TECHNICAL OBJECT OF THE INVENTION

It is therefore the technical object of the invention to provide a non-mammal organism, in particular a microorganism, in which mammal membrane proteins, in particular human membrane proteins, can be functionally expressed in an efficient and simple way.

It is another technical object of the invention to provide a means, which permits in a simple and efficient way the screening of substances or substance libraries for agonists or antagonists of the mammal membrane proteins, in particular the human membrane proteins.

BRIEF DESCRIPTION OF THE DRAWINGS

FIG. 3 shows the gene sequence coding for truncated HMG-CoA reductases (tHMG1).

BASICS OF THE INVENTION AND PREFERRED EMBODIMENTS

For achieving this technical object, the invention teaches inter alia an isolated genetically modified living non-mammal organism, having an increased HMG-CoA reductase activity compared to the wild type, and having a reduced C24 methyltransferase and/or delta22 desaturase activity compared to the wild type, wherein the organism has an increased dehydrocholesterol-delta7 reductase activity compared to the wild type.

The invention is based on the surprising finding that for a functional expression of mammal membrane proteins, i.e. the expression in a folding, which promotes or even at all allows the enzymatic activity of the membrane protein, not only the presence of cholesterol is useful or necessary, but that rather the same success can already be achieved with the presence of desmosterol. Further it has been found that the desmosterol is in fact also located in the (plasma) membrane of the organism. That means that a non-mammal organism is created that has, compared to the wild type, in a membrane, in particular the plasma membrane, an increased content of desmosterol, and if applicable, as will be explained below, of cholesterol. Ultimately, it is achieved by the invention that mammal membrane proteins, in particular human membrane proteins, can be functionally heterologously expressed in not-mammal organisms, for instance in yeasts, by that these organisms are additionally transformed with a gene for the expression of the membrane protein. The membrane proteins can thus be functionally produced in high quantities and in a simple and economical way. This can be further used in manifold ways. Besides the synthesis for production purposes or for structural and/or functional studies, an organism according to the invention can for instance also be used for identifying substances binding to the (functional) membrane protein, for instance by screening. An organism according to the invention is therefore a universal instrument for the functional synthesis of virtually any membrane proteins, for instance plasma membrane proteins, from mammals, such as humans, and for finding agonists and/or antagonists of such membrane proteins. The invention has therefore also special importance as an instrument for finding pharmaceutically suitable substances.

By the genetic modification of the organism with regard to an increased HMG-CoA reductase activity, an increased production of zymosterol is obtained. By the genetic modification with regard to a reduced C24 methyltransferase and/or delta22 desaturase activity, preferably for both, it is achieved that the biosynthesis of ergosterol is blocked or reduced, and that instead by the activities of delta7-delta8 isomerase and delta5 desaturase anyway existing in the organism, together with the introduced delta7 reductase activity, the reaction of zymosterol is catalyzed by cholesta-7-24-dienol and cholesta-5,7,24-trienol to desmosterol.

In an improvement of the invention, it may be provided that the organism additionally has an increased dehydrocholesterol-delta24 reductase activity compared to the wild type. Thereby occurs a further reaction of the desmosterol to cholesterol as well as of the desmosterol precursors cholesta-7,24-dienol and cholesta-5,7,24-trienol to the cholesterol precursors lathosterol and 7-dehydrocholesterol.

It is further preferred that the organism has an increased squalene epoxidase and/or lanosterol demethylase activity compared to the wild type. Thereby, the biosynthesis of zymosterol from squalene is promoted and therefore also the production of desmosterol or cholesterol.

As a non-mammal organism, in principle any organism can be used. The organism may be a prokaryotic organism, in particular selected from the group consisting of bacteria of the species *Bacillus, Escherichia, Lactobacillus, Corynebacterium, Acetobacter, Acinetobacter* and *Pseudomonas*, or a eukaryotic organism, in particular selected from the group consisting of algae of the species Cryptista, Chloromonadophyceae, Xanthophyceae, Crypthecodinium, Chrysophyta, Bacillariophyta, Phaeophyta, Rhodophyta, Chlorophyta, Haptophyta, Cryptista, Euglenozoa, Dinozoa, Chlorarachniophyta, yeasts, insect cells from *Spodoptera frugiperda, Trichoplusia ni, Mamestra brassicae, Drosophila*, and fungi of the species *Aspergillus, Penicillium, Rhizopus, Fusarium, Fusidium, Gibberella, Mucor, Mortierella, Trichoderma* or plants such as peanut, rape, Canola, sunflower, safflower, poppyseed, mustard, hemp, castor oil plant, olive, sesame, Calendula, Punica, primrose, mullein, thistle, wild rose, hazelnut, almond, macadamia nut, avocado, bay, pumpkin, flax, soy, pistachios, borage, trees (oil palm, coconut or walnut) or field crops, such as corn, wheat, rye, oat, triticale, rice, barley, cotton, cassava, pepper, *Tagetes*, Solanaceae plants, such as potato, tobacco, aubergine and tomato, vetches, pea, alfalfa or bush plants (coffee, cocoa, tea), *Salix* genera and perennial grasses and food crops. In the case of a yeast, it may be selected from the group consisting of *Saccharomyces cerevisiae, Saccharomyces delbrückii, Saccharomyces italicus, Saccharomyces ellipsoideus, Saccharomyces fermentati, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum* and *Saccharomycodes ludwigii*, as well as yeasts of the species *Kluyveromyces* such as *K. lactis K. marxianus* var. *marxianus, K. thermotolerans*, and yeasts of the species *Candida* such as *Candida utilis, Candida tropicalis, Candida albicans, Candida lipolytica* and *Candida versatilis*, and yeasts of the species *Pichia* such as *Pichia stipidis, Pichia pastoris* and *Pichia sorbitophila*, and yeasts of the species *Cryptococcus, Debaromyces, Hansenula, Saccharomycecopsis, Saccharomycodes, Schizosaccharomyces, Wickerhamia, Debayomyces, Hanseniaspora, Kloeckera, Zygosaccharomyces, Ogataea, Kuraishia, Komagataella, Metschnikowia, Williopsis, Nakazawaea, Cryptococcus, Torulaspora, Bullera, Rhodotorula, Willopsis* and *Sporobolomyces*, and mosses such as *Physcomitrella* or *Ceratodon*.

The above organism is the basis or a tool for generating an additionally genetically modified organism, which functionally heterologously expresses a mammal membrane protein. Therefore, it is furthermore preferred that the organism additionally is transformed with a gene coding for a membrane protein of a mammal, in particular a human membrane protein, preferably a plasma membrane protein, under the control of a preferably constitutively active promoter. The gene coding for the membrane protein is in principle arbitrary and preferably is selected from the group or family consisting of serotonin transporter gene, noradrenaline transporter gene, dopamine transporter gene, choline transporter gene, glycine transporter gene, gamma-amino acid transporter gene, 5-hydroxytryptamine receptor 3 subunit C, mast/stem cell growth factor receptor precursor, toll-like receptor 8 precursor, similar to olfactory receptor MOR233-18, green-sensitive opsin, glycine receptor, frizzled 5 precursor, dimethylaniline monooxygenase [N-oxide forming], calcitonin gene-related peptide type 1 receptor precursor, muscarinic acetylcholine receptor, C—C chemokine receptor type 4, G protein-coupled receptor, receptor tyrosine kinase, dopamine receptor, substance-K receptor, putative neurotransmitter receptor, thyroid hormone receptor-associated protein complex component TRAP230, fMet-Leu-Phe receptor, gamma-aminobutyric acid receptor alpha-6 subunit precursor (GABA(A) receptor), glucagon-like peptide 2 receptor precursor, G protein-coupled receptor 56, EMR1 hormone receptor, CCK-B/gastrin receptor, alpha-2C-adrenergic receptor, D1beta dopamine receptor, probable G protein-coupled receptor GPR72 precursor, relaxin receptor 2, similar to phospholipase A2 receptor 1, 180 kD, coagulation factor II receptor precursor, somatostatin receptor type 1, acetylcholine receptor protein, alpha chain precursor, interleukin-7 receptor alpha chain precursor, similar to interleukin 9 receptor, similar to transmembrane receptor Unc5H1, ER lumen protein retaining receptor 2, FGF receptor activating protein 1, bone morphogenetic protein receptor type 1B precursor, prolactin receptor precursor, tumor necrosis factor receptor, similar to *Homo sapiens* multiple membrane spanning receptor TRC8 mRNA, feline leukemia virus subgroup C receptor FLVCR, interferon-alpha/beta receptor beta chain precursor, polymeric-immunoglobulin receptor precursor, cell surface glycoprotein receptor CD200, similar to low density lipoprotein receptor-related protein 3, atrial natriuretic peptide receptor B precursor, signal sequence receptor-alpha, protein tyrosine phosphatase, non-receptor type 21, 1-1 receptor candidate protein, probable G protein-coupled receptor GPR37 precursor, interleukin-10 receptor alpha chain precursor, very large G protein-coupled receptor 1, G-protein-coupled receptor HE6 precursor, similar to glutamate receptor delta-1 subunit, retinoic acid receptor gamma-1, similar to olfactory receptor MOR42-1, similar to calcium-sensing receptor related protein 3, autocrine motility factor receptor precursor, class I cytokine receptor, similar to nogo receptor, 5-hydroxytryptamine 6 receptor, tumor necrosis factor receptor super member 1B precursor, polycystic kidney disease and receptor for egg jelly related protein, putative G-protein coupled receptor, sortilin-related receptor precursor, interleukin-12 receptor beta-1 chain precursor, c-type lectin-like receptor-2, similar to olfactory receptor, tumor necrosis factor receptor super member TNFRSF19L precursor, similar to cadherin EGF LAG seven-pass G-type receptor 2, G-protein-coupled receptor, protein tyrosine Phosphatase, receptor type, W, folate receptor alpha precursor, G protein-coupled receptor, similar to olfactory receptor MOR217-1, guanine nucleotide-binding protein-like 1, tumor necrosis factor receptor super member 21 precursor, neuronal acetylcholine receptor protein, alpha-7 chain precursor, interleukin-2 receptor beta chain precursor, cation-dependent mannose-6-phosphate receptor precursor, interleukin-17 receptor precursor, similar to Gamma-aminobutyric acid type B receptor, subunit 2 precursor, interleukin-2 receptor alpha chain precursor, tumor necrosis factor receptor super member 18 precursor, similar to G protein-coupled receptor, C, group 5, similar to MrgG G protein-coupled receptor, interleukin-6 receptor beta chain precursor, lymphatic endothelium-specific hyaluronan receptor LYVE-1, putative G-protein coupled receptor, TGF-beta receptor type III precursor, similar to golgi SNAP receptor complex member 1, high affinity Immunoglobulin epsilon receptor alpha-subunit precursor, interleukin-4 receptor alpha chain precursor, interleukin-12 receptor beta-2 chain precursor, similar to leucocyte immunoglobulin-like receptor-1, similar to P2Y purinoceptor 3 (P2Y3) (Nucleoside diphosphate receptor), tumor necrosis factor receptor super member HA precursor, lymphatic endothelium-specific hyaluronan receptor LYVE-I, activating receptor PILRbeta, ephrin type-A receptor 7 precursor, similar to probable thromboxane A2 receptor isoform beta-human, protein tyrosine Phosphatase, receptor type, C, isoform 2 precursor, endothelial protein C receptor precursor, ATP-binding cassette, sub-B, Putative ATP-binding cassette transporter C13, ATP-binding cassette transporter, ATP-binding cassette, sub-A (ABC1), ATP-binding cassette, sub B, similar to multidrug resistance protein 2, ATP-binding cassette, sub-D, ATP-binding cassette, sub-A, ATP-binding cassette, sub-G, similar to solute carrier 21 (organic anion transporter), organic anion transporter 3, solute carrier 2, (facilitated glucose transporter), solute carrier 7, (cationic amino acid transporter, y+ system), HCAT-2A, solute carrier 6 (neurotransmitter transporter, glycine), sodium-dependent high-affinity dicarboxylate transporter, similar to solute carrier 26, solute carrier 21, UDP N-acetylglucosamine transporter, neutral amino acid transporter B(0), solute carrier 2, facilitated glucose transporter, solute carrier 29 (nucleoside transporters), member 1, solute carrier 26, solute carrier 10 (sodium/bile acid cotransporter), H+/peptide transporter, similar to solute carrier 9, solute carrier 30, solute carrier 25, solute carrier 19 (folate transporter), UDP-glucuronic acid/UDP-N-acetylgalactosamine transporter, solute carrier 16 (monocarboxylic acid transporters), member 4, nucleoside transporter, sodium/nucleoside cotransporter 1, similar to *Mus musculus* putative thymic stromal co-transporter TSCOT mRNA, chromaffin granule amine transporter, acetyl coenzyme A transporter, high affinity choline transporter, organic-cation transporter like, membrane-associated transporter protein, similar to amino acid transporter subunit B0, +AT, similar to non-green plastid triose phosphate translocator precursor, similar to peptide/histidine transporter, Rh type B glycoprotein, sodium/hydrogen exchanger 6, solute carrier 39 (zinc transporter), member 4, peroxisomal Ca-dependent solute carrier, K-CL cotransporter, solute carrier 4, anion exchanger, sodium/iodide cotransporter, Chloride anion exchanger, similar to sodium/potassium/calcium exchanger 3 precursor (Na(+)/K(+)/Ca(2+)-exchange protein 3), sodium dependent phosphate transporter, similar to solute carrier 20 (phosphate transporter, solute carrier 8 (sodium-calcium exchanger), solute carrier 11 (sodium/phosphate symporters), weakly similar to metal homeostasis factor ATX2, iron-regulated transporter IREG1, probable low-affinity copper uptake protein 2, similar to solute carrier 9 (sodium/hydrogen exchanger), isoform 7, voltage-gated sodium channel alpha subunit, potassium channel TASK-4, small conductance calcium-activated potassium channel protein 2, long transient receptor potential channel 2, ether-a-go-go-like potassium channel 1, voltage-gated potassium channel protein, sodium channel, non-voltage-gated 1, delta, voltage-dependent N-type calcium channel, aquaporin, calcium channel, voltage-dependent, alpha, similar to transient receptor potential cation channel, ryanodine receptor 3, transient receptor potential cation channel, potassium channel sub K, cyclic nucleotide gated channel alpha, similar to *Rattus norvegicus* potassium channel regulator 1 mRNA, similar to chloride channel protein 3 (ClC-3), calcium-activated chloride channel-2, lens fiber membrane intrinsic protein, sperm ion channel, similar to Shaw-related potassium channel protein Raw1, dihy-dropyridine-sensitive L-type, calcium channel alpha-2/delta subunits precursor, similar to voltage-dependent anion channel 2, mid-1-related chloride channel, similar to potassium channel subunit (Slack), ATPase, Ca++ transporting, fast twitch 1, plasma membrane calcium-transporting, vacuolar proton translocating ATPase 116 kDa subunit A, sodium/potassium-transporting ATPase alpha-3 chain, copper-transporting ATPase 1 (Copper pump 1) (Menkes disease-associated protein), probable cation-transporting ATPase 3 (fragment), vacuolar ATP synthase subunit S1 precursor, similar to potential phospholipid-transporting ATPase ID, sodium/potassium-transporting ATPase beta-3 chain, tyrosine kinase, protein-tyrosine phosphatase, non-receptor type 5, putative transmembrane GTPase (fragment), epidermal growth factor (beta-urogastrone), protein kinase C-like 1, weakly similar to RAS suppressor protein 1, dioxin receptor repressor, cAMP-specific 3',5'-cyclic phosphodiesterase 4A, MAP-kinase activating death domain-containing protein, isoform g, ras guanine nucleotide exchange factor 2 (fragment), NADPH-dependent FMN and FAD containing oxidoreductase, dolichyl-diphosphooligosaccharide-protein glycosyltransferase 63 kDa subunit precursor, phosphatidylinositol glycan, class B, A kinase (PRKA) anchor protein 13, 85 kDa calcium-independent phospholipase A2, A-Raf proto-oncogene serine/threonine-protein kinase, similar to peptidylprolyl isomerase A (cyclophilin A), Ras-related GTP-binding protein, similar to sphingosine-1-phosphate phosphatase 1, WNT-10A protein precursor, similar to ADP-ribosylation factor-like 1, transforming growth factor alpha precursor, guanine nucleotide exchange factor, protein-tyrosine phosphatase, non-receptor, similar to putative serine/threonine protein kinase, calcium/calmodulin-dependent protein kinase type IV catalytic chain, similar to phosphatidylinositol-4-phosphate 5-kinase, type II, gamma, similar to 52 kDa repressor of the inhibitor of the protein kinase (p58IPK-interacting protein) (58 kDa interferon-induced protein kinase-interacting protein) (P52rIPK) (death associated protein 4), apoptosis regulator, SH2 domain-containing Phosphatase anchor protein 1, similar to RHO-GAP hematopoietic protein Cl, similar to phosphatidylinositol 3-kinase delta catalytic subunit, similar to tumor-associated calcium signal transducer 1 precursor (major gastrointestinal tumor-associated protein GA733-2) (epithelial cell surface antigen) (epithelial glycoprotein) (EGP) (adenocarcinoma-associated antigen) (KSA) (KS 1/4 antigen), proto-oncogene tyrosine-protein kinase ROS precursor, membrane-bound transcription factor site 2 protease, inositol polyphosphate 5-phosphatase, microsomal signal peptidase 25 kDa subunit, similar to AMP-activated protein kinase gamma subunit, tumor necrosis factor ligand super member 8, sterol regulatory element binding protein cleavage-activating protein, transmembrane protease, serine 3, isoform 3, similar to Ser-Thr protein kinase related to the myotonic dystrophy protein kinase, membrane-bound transcription factor site-1 protease precursor, similar to 52 kDa repressor of the inhibitor of the protein kinase (p58IPK-interacting protein) (58 kDa interferon-induced protein kinase-interacting protein) (P52rIPK) (death associated protein 4), PAS-kinase, serine/threonine protein phosphatase 2B catalytic subunit, alpha isoform, signal transduction protein CBL, rab proteins geranylgeranyltransferase component A 2, similar to Rho-interacting protein 2 (Rho-guanine nucleotide exchange factor) (RhoGEF) (RIP2), pre-mRNA splicing factor ATP-dependent RNA helicase PRP16, splicing factor 3b, subunit 1, 155 kD, SP110 nuclear body protein, isoform a, similar to SMC2 structural maintenance of chromosomes 2-like 1

(yeast), similar to polymerase (DNA directed), theta, nuclear factor 1/B, nurim (nuclear envelope membrane protein), similar to nuclear receptor coactivator 4, weakly similar to splicing factor, arginine/serine-rich 4, similar to elongation factor 1-alpha 1 (EF-1-alpha-1) (elongation factor 1 A-1) (eEF1A-1) (elongation factor Tu) (EF-Tu), similar to 6OS ribosomal protein L7, deoxyribonuclease II alpha putative, nuclear factor of kappa light polypeptide gene enhancer in B cells inhibitor, epsilon, solute carrier 25 (mitochondrial carrier), similar to cytochrome b-561, cytochrome oxidase subunit I, succinyl-CoA ligase [GDP-forming] beta-chain, mitochondrial precursor (fragment), similar to cytochrome oxidase biogenesis protein OXA1, mitochondrial precursor (OXA1-like protein) (OXA1Hs), NADH-ubiquinone oxidoreductase chain 5, trifunctional enzyme beta subunit, mitochondrial precursor, methylcrotonyl-CoA carboxylase beta chain, mitochondrial precursor, similar to cytochrome c oxidase subunit III, putative ATP-dependent CIp protease proteolytic subunit, mitochondrial precursor, NADH-ubiquinone oxidoreductase 39 kDa subunit, mitochondrial precursor, second mitochondria-derived activator of caspase, isoform Smac-delta, precursor, similar to NADH dehydrogenase subunit 5, mitochondrial import inner membrane translocase subunit TIM23, similar to cytochrome b, mitochondrial precursor proteins import receptor, cytochrome c oxidase polypeptide II, short chain 3-hydroxyacyl-CoA dehydrogenase, mitochondrial precursor, similar to 60 kDa heat shock protein, mitochondrial precursor (Hspβ0), Cytochrome c1, heme protein, mitochondrial precursor, protoheme IX farnesyltransferase, mitochondrial precursor, glycerol-3-phosphate dehydrogenase, mitochondrial precursor, homeobox protein Hox-A7, transcriptional regulator ATRX, similar to general transcription factor II, i, isoform 1, similar to general transcription factor IIIC, polypeptide 1 (alpha subunit, 220 kD), transcriptional activator SRCAP, sterol/retinol dehydrogenase, alkaline phytoceramidase, carnitine 0-palmitoyltransferase I, mitochondrial liver isoform, similar to bA84N7.1 (novel protein similar to diacylglycerol kinase eta (DGKH)), 1-acyl-sn-glycerol-3-phosphate acyltransferase epsilon, mannose-P-dolichol utilization defect 1 protein, sterol O-acyltransferase 2, apolipoprotein L1 precursor, phosphatidylcholine-sterol acyltransferase precursor, fatty acid hydroxylase, moderately similar to *Mus musculus* putative lysophosphatidic acid acyltransferase mRNA, weakly similar to phospholipase A2 inhibitor subunit B precursors, phosphatidylinositol-glycan biosynthesis, class F protein, serine palmitoyltransferase 1, phosphatidylserine synthase I, similar to 1-acyl-sn-glycerol-3-phosphate acyltransferase gamma (1-AGP acyltransferase 3) (1-AGPAT 3) (lysophosphatidic acid acyltransferase-gamma) (LPAAT-gamma) (1-acylglycerol-3-phosphate O-acyltransferase 3), similar to triacylglycerol lipase, gastric precursor (Gastric lipase) (GL), 3-hydroxy-3-methylglutaryl coenzyme A reductase, ceramide glucosyltransferase, dolichyl-P-Man:Man (5) GIcNAc (2)-PP-dolichyl mannosyltransferase, N-acetylglucosaminyl-phosphatidylinositol de-N-acetylase, dolichyl-diphosphooligosaccharide-protein glycosyltransferase 67 kDa subunit precursor, diacylglycerol kinase, zeta, apolipoprotein F, similar to fatty acid amide hydrolase, similar to long-chain-fatty-acid-CoA ligase 6 (LACS 6), farnesyl pyrophosphate synthetase (FPP synthetase), sphingomyelin phosphodiesterase 2, neutral membrane (neutral sphingomyelinase), estradiol 17 beta-dehydrogenase 7, phosphatidyl inositol glycan class S, 24-dehydrocholesterol reductase precursor, oxysterol-binding protein 1, 1-acyl-sn-glycerol-3-phosphate acyltransferase beta, myo-inositol-1 (or 4)-monophosphatase, estradiol beta-dehydrogenase7, 1-acyl-sn-glycerol-3-phosphate acyltransferase beta, putative fatty acid desaturase MLD, CDP-diacylglycerol-inositol 3-phosphatidyltransferase, lysosomal apyrase-like protein 1, acyl-malonyl condensing enzyme, ubiquitin-conjugating enzyme E2, thyroid peroxidase precursor (2 members), UDP-N-acetylglucosamine-dolichyl-phosphate N-acetylglucosaminephosphotransferase, N-acetylglucosamine-1-phosphodiester alpha-N-acetylglucosaminidase, 3 beta-hydroxysteroid dehydrogenase/delta 5→4-isomerase type II, similar to adenylate cyclase 6, isoform a, similar to cytochrome P450 IID6, Ga1NAc 4-sulfotransferase, GPI transamidase, proprotein convertase subtil-isin/kexin type 7, NEDD4-like ubiquitin ligase 1, hyaluronan synthase 2, ketohexokinas, testis ecto-ADP-ribosyltransferase precursor, alkaline phosphatase, intestinal precursor, 5,6-dihydroxyindole-2-carboxylic acid oxidase precursor, biotin-protein ligase, dolichyl-diphosphooligosaccharide-protein glycosyltrans ferase, squalene monooxygenase, ubiquitin specific protease, similar to glycerol kinase, probable dolichyl pyrophosphate Glc1Man9G1cNAc2 alpha-1,3-glucosyltransferase, gamma-glutamyltranspeptidase 1 precursor, serine hydrolase-like protein, phosphatidate cytidylyltransferase 2, DNA topoisomerase II, beta isozyme, lysosomal acid phosphatase precursor, muscle-specific DNase I-like precursor, similar to kynurenine 3-monooxygenase, similar to peptidylglycine alpha-amidating monooxygenase, N-acetylglucosamyl transferase component GPI1, similar to cGMP-inhibited 3,5-cyclic phosphodiesterase A (cyclic GMP inhibited phosphodiesterase A) (CGI-PDE A), beta-1,4 mannosyltransferase, cholinephosphotransferase 1, moderately similar to *Homo sapiens* neuropathy target esterase, CAAX prenyl protease 1 homolog, pantothenate kinase 1alpha, similar to N-acetylglucosaminyltransferase VI, cytochrome P450 39A1, similar to glyceraldehyde 3-phosphate dehydrogenase, liver, similar to beta-1,4 N-acetylgalactosaminyltransferase, CAAX prenyl protease 2, beta-1, 3-galactosyltransferase-6, hexosaminidase A, carbonic anhydrase-related protein 2 precursor, vitamin K-dependent gamma-carboxylase, malate dehydrogenase, cytoplasmic, mannosyltransferase, long form of N-acetylglucosamine-6-0-sulfotransferase, sialic acid-specific acetylesterase II, similar to uracil DNA glycosylase, beta-hexosaminidase beta chain precursor, similar to L-lactate dehydrogenase B chain (LDH-B), probable serine protease HTRA3 precursor, weakly similar to UDP-N-acetyl-glucosamine-peptide N-acetylglucosaminyltransferase 110 kDa subunit, neutral sphingomyelinase II, similar to putative N-acetyltransferase Camello 2, weakly similar to NADPH-cytochrome P450 reductase, similar to ecto-nucleotide pyrophosphatase/phosphodiesterase 5, similar to 3-0X0-5-alpha-steroid 4-dehydrogenase 2, blood plasma glutamate carboxypeptidase precursor, xylosyltransferase II, casein kinase I, epsilon isoform, selenide, water dikinase 2, paraoxonase 2, similar to NADH-ubiquinone oxidoreductase MLRQ subunit, similar to ADAMTS-5 precursor (A disintegrin and metalloproteinase with thrombospondin motifs 5) (ADAM-TS 5) (ADAM-TS5) (aggrecanase-2) (ADMP-2) (ADAM-TS 11), galactose-3-0-sulfotransferase, valyl-tRNA synthetase 2, ribonuclease H1, acetyl-CoA carboxylase 2, similar to alpha-L-iduronidase precursor, similar to ADAMTS-5 precursor (A disintegrin and metalloproteinase with thrombospondin motifs 5) (ADAM-TS 5) (ADAM-TS5) (Aggrecanase-2) (ADMP-2) (ADAM-TS 11), Kunitz-type protease inhibitor 1 precursor, putative sialo-glycoprotease type 2, ubiquitin-activating enzyme E1 homolog, prenylcysteine lyase precursor, dimeric dihydrodiol dehydrogenase, glycosyltransferase, integrin alpha-V precursor, axonemal dynein heavy chain (fragment), cop-coated vesicle membrane protein p24 precursor, protocadherin ARCADLIN, keratin, type I cytoskeletal, nuclear envelope pore membrane protein, gamma-tubulin complex component 6, cleft lip and palate associated transmembrane protein 1, Sec61 homolog, presenilins associated rhomboid-like protein, putative prostate cancer tumor suppressor, signal recognition particle receptor ('docking protein'), HLA class I histocompatibility antigen, B-8 B*0801 alpha chain precursor, weakly similar to peregrine, HLA class II histocompatibility antigen, beta chain precursor, kit ligand precursor, Ret finger protein 2, ASPP1 protein, neuronal membrane glycoprotein M6-a, membrane cofactor protein (CD46, trophoblast-lymphocyte cross-reactive antigen), vesicle trafficking protein, epithelial membrane protein-1, neurexin 3-beta precursor, intercellular adhesion molecule-3 precursor, presenilin 2, BCL2/adenovirus E1B 19-kDa protein-interacting protein 2, corticosteroid-binding globulin precursor, T-cell surface glycoprotein CD8 alpha chain precursor, capillary morphogenesis protein-2 precursor, trans-golgi network protein 2, bax inhibitor-1, yang-like 1 (van Gogh, *Drosophila*), tuberous sclerosis 2 isoform 2, P protein, down syndrome cell adhesion molecule precursor, vascular cell adhesion protein 1 precursor, clathrin assembly lymphoid myeloid leukemia protein, kelch-like protein 2, myeloid/lymphoid or mixed-lineage leukemia (trithorax homolog, *Drosophila*), transmembrane 4 super, microtubule-associated protein 1A, tetraspanin, synaptotagmin XI, spinster-Like protein, integrin beta 1 isoform 1A precursor, weakly similar to patched protein homolog 1, pro-neuregulin-2 precursor, tumor metastasis-suppressor, sel-1 homolog precursor, 150 kDa oxygen-regulated protein precursor, mu-protocadherin related protein splice variant, weakly similar to protein PTM1 precursor, weakly similar to cochlin precursor, similar to TRAM protein (translocating chain-associating membrane protein), COPS complex subunit 7A, calcium binding atopy-related autoantigen 1, similar to metaxin 1, envelope protein precursor, protein associated with Myc, ocular albinism type 1 protein, PL6 protein, unknown function but deleted in small cell lung cancer (fragment), tumor endothelial marker 5 precursor, tumor suppressor protein DCC precursor, mucin, tumor endothelial marker 7-related precursor, zinc finger protein 179, alpha integrin binding protein 63, similar to Stromal interaction molecule 1 precursor, similar to *Homo sapiens* squamous cell carcinoma antigen recognized by T cell, P400 SWI2/SNF2-related protein, NgCAM-related related cell adhesion molecule (fragment), similar to transmembrane protein induced by tumor necrosis factor alpha, similar to Apobec-1 complementation factor, APOBEC-1 stimulating protein, malignant cell expression-enhanced gene/tumor progression-enhanced gene, putative ferritin (fragment), weakly similar to human DHHC-domain-containing cysteine-rich protein mRNA, similar to multiple endocrine neoplasia I, similar to HIRA protein (TUP1 like enhancer of split protein 1), envelope protein, transmembrane 7 super protein member 3 precursor, bladder cancer overexpressed protein, transmembrane protein vezatin, golgi apparatus protein 1 precursor, vascular non-inflammatory molecule 2 precursor, E-selectin precursor, myeloid cell surface antigen CD33 precursor, similar to FH1/FH2 domains-containing protein (formin homolog overexpressed in spleen) (FHOS), patched protein homolog 1, pannexin 3, scleroderma-associated autoantigen, ecotropic viral integration site 2B, alpha-sarcoglycan precursor, hematopoietic progenitor cell antigen CD34 precursor, hepatocellular carcinoma-associated antigen 112, neuropilin 1, basigin precursor, pregnancy-associated plasma preproprotein-A2, basement membrane-specific heparan sulfate proteoglycan core protein precursor, high-risk human papilloma viruses E6 oncoproteins targeted protein E6TP1 beta, highly similar to *Rattus norvegicus* db83 mRNA, transducin-like enhancer protein 2, protocadherin fat 2, Unc-93 related protein, retino-blastoma-associated factor 600, CD44 antigen (homing function and Indian blood group system), meprin A alpha-subunit precursor, similar to podocalyxin-like protein 1 precursor, similar to *Mus musculus* ganglioside-induced differentiation associated protein 1, leucine-rich repeat protein LRRC3 precursor, endothelial and smooth muscle cell-derived neuropilin-like protein, source of immunodominant MHC-associated peptides, fibulin 2 precursor, CD3Z antigen, zeta polypeptide, T-cell surface glycoprotein CD3 gamma chain precursor, pancreatic secretory granule membrane major glycoprotein GP2 precursor, signaling lymphocytic activation molecule precursor, Alzheimer's disease amyloid A4 protein precursor, protein pM5 precursor, similar to dynein light chain-A, lymphocyte-activation protein 3 precursor, progressive ankylosis protein homolog, erythrocyte band 7 integral membrane protein, SYG1 protein, similar to SYNAPSINS IA and IB, similar to amyotrophic lateral sclerosis 2 (juvenile) chromosome region, candidate 2, polycystic kidney disease 1 protein, Niemann-Pick Cl protein precursor, DNAJ protein homolog 1, thrombomodulin precursor, weakly similar to occluding, occludin, similar to rennin, junctophilin type3, similar to homeotic protein CHox3-chicken, similar to glycolipid transfer protein (GLTP), proteasome subunit alpha type, extracellular matrix protein, delta-sarcoglycan, prominin-like protein 1 precursor, translocon-associated protein, delta subunit precursor, peroxisome biogenesis factor 1, neuroglycan C, SH3 adapter protein SPIN90, Mcd4p homolog, T lymphocyte activation antigen CD80 precursor, similar to calcium-binding protein CaBP7, tight junction protein ZO-I, dysferlin, dachshund 2, barttin, T-cell surface glycoprotein CD5 precursor, brain specific membrane-anchored protein precursor, similar to fatty acid-binding protein, heart (H-FABP) (muscle fatty acid-binding protein) (M-FABP) (mammary-derived growth inhibitor) (MDGI), peroxisome assembly factor-1, pentaxin-related protein PTX3 precursor, neuropilin and tolloid like-1, cat eye syndrome critical region protein 6, peptidoglycan recognition protein-I-alpha precursor, signal recognition particle receptor beta subunit, similar to ra1A binding protein 1, T-cell surface protein tactile precursor, transmeitibrane gamma-carboxyglutamic acid protein 4 precursor, JAW1-related protein MRVI1A long isoform, peroxisomal membrane protein PEX13, zona pellucida sperm-binding protein 2 precursor, similar to proteasome (prosome, macropain) subunit, beta type, 3, cell surface glycoprotein MUC18 precursor, similar to golgi autoantigen, golgin sub a, 2, ISS~homolog to INHIBITOR OF CARBONIC ANHYDRASE PRECURSOR-putative, similar to alpha-2 catenin (alpha-catenin related protein) (alpha N-catenin), sterol regulatory element binding protein-1, similar to transcription elongation factor S-II (transcription elongation factor A), protocadherin 15 precursor, homolog of *DROSOPHILA* HEADCASE, calmin, oxysterol binding protein-related protein 8, nesprin-1 alpha, SOX-13 protein, DNA-directed RNA polymerase I largest subunit, ANTHRACYCLINE-associated resistance ARX, similar to matrin 3, blood vessel epicardial substance, wolframin, fibroblast growth factor-4 precursor, noggin precursor, transcobalamin I precursor, of Willebrand factor precursor, laminin beta-3 chain precursor, similar to CAP-binding protein complex interacting protein 2, calsyntenin-2, brother of CDO, hepatocellular carcinoma-associated antigen 137, testis-specific protein TEX28, megakaryocyte-enhanced gene transcript 1 protein, similar to vitelliform macular dystrophy (Best disease, bestrophin), similar to integrin alpha-2b chain precursor-human, mucin 2 precursor, male-specific lethal-3 homolog 1, protocadherin Flamingo 2, STRA6 isoform 1, cystinosin, ELK4 protein, isoform b, similar to apoptosis regulator bcl-x isoform-human, endoglin precursor, similar to 1 beta dynein heavy chain, similar to WNT-5A protein precursor, similar to H3.3 like histone MH321-mouse, MHC class II regulatory factor RFX1, sarcospan, mandaselin long form, matrilin-2 precursor, similar to DESC1 protein, interphotoreceptor matrix proteoglycan 200, inhibin alpha chain precursor, interphotoreceptor matrix proteoglycan 200, male-specific lethal-3 homolog 1, nephrin precursor, matrilin-2 precursor, M130 antigen cytoplasmic variant 2 precursor, cleavage and polyadenylation specificity factor, 160 kDa subunit, blood vessel epicardial substance, transmembrane 6 super member 2 (fragment), similar to Zinc finger protein HRX (ALL-I) (trithorax-like protein), NgCAM-related related cell adhesion molecule (fragment), polycystin-1L1, similar to dynamin-1, similar to OTK27, platelet glycoprotein Ib beta chain precursor, NMD protein, intersectin 2, matrilin-2 precursor, ERGIC-53 protein precursor, translocon-associated protein, gamma subunit, weakly similar to zinc/cadmium resistance protein, quiescin, similar to prot GOR, megakaryocyte-enhanced gene transcript 1 protein.

Gene sequences coding for suitable HMG-CoA reductases, including truncated, but still functional HMG-CoA reductases such as tHMG1, are known for instance from the following Acc.-Nos. of the gene database of The National Center for Biotechnology Information (NCBI): NC_001145, NM_106299, NC_003421.2, NC_009784.1, NC_003028.3, NC_007308.3, and FIG. 3 (tHMG1).

Gene sequences coding for C24 methyltransferases to be inhibited are known for instance from the following Acc.-Nos. of the gene database of The National Center for Biotechnology Information (NCBI): NC_001145, NC_000911.1, NC_003423.3.

Gene sequences coding for delta22 desaturases to be inhibited are known for instance from the following Acc.-Nos. of the gene database of The National Center for Biotechnology Information (NCBI): NC 003424.3, NC 009046.1, NC 001145.2.

Gene sequences coding for suitable delta7 reductases are known for instance from the following Acc.-Nos. of the gene database of The National Center for Biotechnology Information (NCBI): NM_103926, NM_001360, NM_007856, NM_203904, NM_001014927, NM_201330, NM_022389, NM_001131727, NM_001087087, XM_001497598, XM_001174160, XM_001099101, BM490402, CA753545.

Gene sequences coding for suitable delta24 reductases are known for instance from the following Acc.-Nos. of the gene database of The National Center for Biotechnology Information (NCBI): NM_014762, NM_001016800, NM_001094456, NM_001008645, NM_001103276, NM_001080148, NM_053272, NM_00103128, XM_001488247, AB125202, XM_001153751.

Gene sequences coding for suitable delta7-delta8 isomerases are known for instance from the following Acc.-No. of the gene database of The National Center for Biotechnology Information (NCBI): M74037.

Gene sequences coding for suitable delta5 desaturases are known for instance from the following Acc.-Nos. of the gene database of The National Center for Biotechnology Information (NCBI): S46162, NG_009446, NM_053642, NM_001035356.

Gene sequences coding for suitable squalene epoxidases are known for instance from the following Acc.-No. of the gene database of The National Center for Biotechnology Information (NCBI): M64994.

Gene sequences coding for suitable lanosterol demethylases are known for instance from the following Acc.-No. of the gene database of The National Center for Biotechnology Information (NCBI): EF059165.

Gene sequences coding for exemplary heterologously expressible mammal membrane proteins are known for instance from the following Acc.-Nos. of the gene database of The National Center for Biotechnology Information (NCBI): NP_570126, NP_006019, NP_000860, NP_619542, NP_000786, NP_000787, NP_150645, NP_150646, NP_057658, NP_387512, NP_000669, NP_150647, NP_000671, NP_387507, NP_387508, NP_387509, NP_000670, NP_001690, NP_068713. Further gene sequences for mammal membrane proteins, in particular for the membrane proteins listed above, can easily be identified by research in the mentioned gene database.

Gene sequences coding for suitable promoters (promoters of the respective heterologously expressed enzymes and/or proteins may be respectively identical or different in an organism according to the invention) are known for instance from the following Acc.-Nos. of the gene database of The National Center for Biotechnology Information (NCBI): NC_001142, NC_001139, NC_001147, NC_001139, NC_001148, NC_001135, NC_001136.

An enzymatic activity in an organism according to the invention is increased, compared to the wild type, if the activity is at least by 10%, preferably at least by 50%, most preferably at least by 1,000% higher than the same activity in the corresponding wild type. The term increase also comprises the presence of the respective enzymatic activity in an organism according to the invention, if the corresponding wild type does not have any identical activity.

An enzyme has HMG-CoA reductase activity, if it is capable to catalyze the reaction of beta-hydroxy-beta-methylglutaryl coenzyme A to mevalonate.

An enzyme has C24 methyltransferase activity, if it is capable to catalyze the reaction of zymosterol to fecosterol.

An enzyme has delta22 desaturase activity, if it is capable to catalyze the reaction of ergosta-5,7,24(28)-trienol to ergosta-5,7,22,24(28)-tetraenol.

An enzyme has dehydrocholesterol-delta7 reductase (in short: delta7 reductase) activity, if it is capable to catalyze the reaction of cholesta-5,7,24-trien-3-ol to desmosterol.

An enzyme has dehydrocholesterol-delta24 reductase (in short: delta24 reductase) activity, if it is capable to catalyze the reaction of cholesta-7-24-dien-3beta-ol to lathosterol, of cholesta-5,7,24-trien-3-ol to 7-dehydrocholesterol, and/or of desmosterol to cholesterol.

An enzyme has squalene epoxidase activity, if it is capable to catalyze the reaction of squalene to squalene epoxide.

An enzyme has lanosterol demethylase activity, if it is capable to catalyze the reaction of lanosterol to 4,4-dimethylcholesta-8,14,24-trienol.

An enzyme has delta7-delta8 isomerase activity, if it is capable to catalyze the reaction of fecosterol to episterol, and/or of zymosterol to cholesta-7-24-dien-3-beta-ol. Such an enzyme is preferably expressed in the wild type of the organism according to the invention already. If the wild type of this enzyme is not or not to a sufficient degree expressed, the organism according to the invention can be transformed with a gene coding for this enzyme, under the control of a preferably constitutively active promoter.

An enzyme has delta5 desaturase activity, if it is capable to catalyze the reaction of episterol to ergosta-5-7-24(28), of cholesta-7-24-dien-3-beta-ol to cholesta-5,7,24-trien-3-ol, and/or of lathosterol to 7-dehydrocholesterol. Such an enzyme is preferably expressed in the wild type of the organism according to the invention already. If the wild type of this enzyme is not or not to a sufficient degree expressed, the organism according to the invention can be transformed with a gene coding for this enzyme, under the control of a preferably constitutively active promoter.

Generally, an enzymatic activity mentioned above is measured by that a given amount of the respective educt is reacted to the product under addition of a given amount of the respective enzyme and if applicable given amounts of the other necessary reaction partners, and the amount of the product formed in a given time is determined.

The determination of the HMG-CoA reductase activity, the lanosterol demethylase activity, the squalene epoxidase activity, the C24 methyltransferase activity, the delta7-delta8 isomerase activity, the delta5 desaturase activity, the delta 22 desaturase activity and the delta24 reductase activity is made for instance as described in the document WO 03/064650 A1. The determination of the delta7 reductase activity is made in analogous manner.

The content of desmosterol and/or cholesterol is increased in a membrane, in particular a plasma membrane, of an organism according to the invention compared to the wild type, if the amount of the respective substance is at least by 10%, preferably at least by 50%, most preferably at least by 1,000% higher than the same activity in the corresponding wild type. The term increase also comprises the presence of the respective substance in the membrane of an organism according to the invention, if the substance cannot be detected in the membrane of a corresponding wild type. The measurement of the amount is performed as mentioned in the examples under the headings "Processing of the membrane sterols" and "Conditions for the gas chromatography (GC)".

The invention further teaches the use of an organism according to the invention for the production of desmosterol and/or cholesterol, the organism preferably being aerobically cultivated. The suitable cultivation conditions for a certain organism are well known to the man skilled in the art.

Another use of an organism according to the invention teaches the production of a membrane protein of a mammal, in particular of a human membrane protein, preferably of a plasma membrane protein, and is characterized in that the organism transformed with a gene coding for a membrane protein of a mammal is cultivated, preferably without addition of cholesterol and/or desmosterol, and that after expiration of a given cultivation time the membrane protein is isolated from a cultivation supernatant and/or from the organism.

Another use of an organism according to the invention relates to the screening for substances binding to a membrane protein of a mammal, in particular to a human membrane protein, preferably to a plasma membrane protein, wherein the organism transformed with the gene for the membrane protein or a membrane extract of the transformed organism, if applicable after previous cultivation of the organism, is contacted with a given substance or a mixture of given substances, that modifications or absence of modifications of properties of the organism, of the membrane extract, and/or of the binding or non-binding of a substance to the membrane protein is measured, and that with measurement of modifications and/or binding, the substance or the mixture of substances is categorized as binding to the membrane protein. To the properties to be determined of the organism belong the determination of the viability, the quantitative determination of the cell growth and the quantitative determination of given metabolic products of the cells after expiration of a given time of contact with a prospective substance or a prospective mixture of substances and the comparison of the determined parameter with the same parameter before contacting. The binding of a prospective substance to a membrane protein can be made with all conventional binding assays. For this purpose, it may be provided that the membrane protein and/or the substance is covalently bound to a reporter molecule detectable by means of physical, physicochemical or chemical methods.

The invention further relates to a kit for carrying-out a screening method according to the invention. It contains an organism according to the invention, optionally a nucleic acid construct suitable for the transformation of the organism and containing a nucleic acid coding for a membrane protein of a mammal, in particular a human membrane protein, preferably a plasma membrane protein, which is under the control of a preferably constitutively active promoter, and instructions of use for transforming the organism with the nucleic acid construct contained or separately made available, for cultivating the organism before and after the transformation, for contacting the organism with a given substance or a given mixture of substances, and for measuring a modification of a property of the organism and/or a binding of the substance or mixture of substances to the membrane protein.

Subject matter of the invention is further a nucleic acid construct, in particular plasmid or shuttle vector, containing a nucleic acid or several nucleic acids, identical or different, coding for a protein with dehydrocholesterol-delta7 reductase activity and/or dehydrocholesterol-delta24 reductase activity, wherein the nucleic acid(s) is or are (respectively) under the control of a preferably constitutively active promoter. The nucleic acid construct may additionally contain: a nucleic acid or several nucleic acids, identical or different, coding for a protein with HMG-CoA reductase and/or squalene epoxidase and/or lanosterol demethylase activity, wherein the nucleic acid(s) is or are (respectively) under the control of a preferably constitutively active promoter.

Such a nucleic acid construct can be used for producing an organism according to the invention, wherein a precursor organism, with which the nucleic acid construct is transformed, wherein the precursor organism preferably is a genetically modified organism having a reduced C24 methyltransferase and/or a delta22 desaturase activity compared to the wild type.

Finally, the invention relates to a membrane extract, in particular plasma membrane extract, obtainable from an organism according to the invention by digestion of the organism and separation of the membrane, in particular the plasma membrane. Suitable methods for the digestion or for the separation and isolation of the membrane are well known to the man skilled in the art.

All above and following explanations and preferred variants to an aspect of the invention are correspondingly used for the other aspects of the invention, without the need to explicitly repeat the respective features of each aspect of the invention. All disclosed features can be combined in an arbitrary manner with various aspects of the invention, irrespective of in which context the features are specifically disclosed.

The contents of all cited documents and sources, in particular the referred-to Accession Numbers of gene databases and methods of the determination of activities, are part of the present specification ("incorporated by reference"), without the need to explicitly repeat the contents here.

In the following, the invention is described in more detail with reference to examples.

Example 1: Used Materials and Methods 1.1: Primers.

All primers were synthesized by the company Metabion (Martinsried).

TABLE 1

PCR primers for amplification.
The recognition sequences for the restriction enzymes NotI and XhoI are underlined.

| Primer | Sequence |
|---|---|
| mSERTNotIf | 5'-AT<u>GCGGCCGC</u>ACCATGGAGACCACACCTTTG-3' |
| mSERTXhoIr | 5'-AT<u>CTCGAG</u>TTACACAGCATTCATGCGG-3' |

1.2: Plasmids.

pFlat vector system (Veen, M., dissertation, TU Berlin (2002)).

In the following experiments, different strains of the yeast *S. cerevisiae* were transformed with the pFlat1 or pFlat3 vector of the pFlat vector system (Jacobs B L, Azmitia E C. Physiol Rev (1992) 72, 165-229). These *E. coli* ⇌ *S. cerevisiae* "shuttle vectors" comprise a NotI and a XhoI restriction site in the "Multiple cloning site", which were used in the present work for cloning. Furthermore, these plasmids carry the LEU2 (pFlat3) or the URA3 gene (pFlat1), respectively, which are used as auxotrophy marker genes for the selection of plasmid-carrying strains on corresponding minimal media.

pCis-rSERT.

The eukaryotic expression vector pCis contains the cDNA of the rat serotonin transporter, which was integrated between the restriction sites XhoI and HpaI.

1.3: Strains.

*Escherichia coli* K12 JM109.

[recA1 endA1 gyrA96 thi hsdR17 supE44 λ⁻relA1 Δ(lac-proAB)/F' traD36 proA⁺B⁺lacI$^q$lacZΔM15].

(Yanisch-Perron, C., Vieira, J., Messing, J. Gene (1985) 33 (1), 103-119).

*Saccharomyces cerevisiae* GRFura3.

[MATa leu2-3, leu2-112, his4-519, can1, ura3Δ].

(Veen, 2002, see above).

*Saccharomyces cerevisiae* GRFco1.

[MATa tHMG1-leu2, ERG1-erg5, ERG11-erg6, his3, ura3, can1]. (Veen, 2002, see above).

1.4: Media.

LB Medium:

1% tryptone; 0.5% yeast extract; 0.5% NaCl; pH 7.4.

YE Medium:

0.5% yeast extract; 2% glucose; pH 6.3.

YNB Medium:

0.67% YNB ("yeast nitrogen base", Difco, Augsburg); 2% glucose.

WMVIII:

(Lang and Looman, see above)—For 1 liter medium: 50 g saccharose; 250 mg $NH_4H_2PO_4$; 2.8 $NH_4Cl$; 250 mg $MgCl_2\times 6H_2O$; 100 mg $CaCl_2\times 2H_2O$; 2 g $KH_2PO_4$; 550 mg $MgSO_4\times 7H_2O$; 75 mg meso-inositol; 10 g Na-glutamate; 1 ml 1000× trace elements solution; 4 ml 250× vitamin solution.

Trace Elements:

1000× concentrated: 1.75 g $ZnSO_4\times 7H_2O$; 0.5 g $FeSO_4\times 7H_2O$; 0.1 g $CuSO_4\times 5H_2O$; 0.1 g $MnCl_4\times 4H_2O$; 0.1 g $NaMoO_4\times 2H_2O$ for 1 liter.

Vitamin Solution:

250× concentrated: 2.5 g nicotinic acid; 6.25 g pyridoxine; 2.5 g thiamine; 0.625 g biotin; 12.5 g Ca pantothenate for 1 liter.

For agar plates, 1.5% agar (Serva, Heidelberg) were added to the medium.

Antibiotics:

Ampicillin (Boehringer, Mannheim) 50 µg/ml.

Media Supplements:

Leucine (0.4 g/l); histidine-HCl (20 mg/l).

1.5: Buffers and Chemicals.

Laemmli buffer (4×):

0.2 M tris-HCl pH 6.8; 8% SDS; 0.4% bromphenol blue; 40% glycerol; 400 mM DTT; 4% Triton-X.

PBS ("Phosphate-Buffered Saline"):

150 mM NaCl; 8.4 mM $Na_2HPO_4$; 1.6 mM $KH_2PO_4$, pH 7.4.

PBS-T:

1×PBS pH 7.4; 0.05% Tween 20.

Stopper Solution (4×):

60% (w/v) saccharose; 20 mM EDTA; 0.025% (w/v) bromphenol blue.

TAE Buffer:

20 mM sodium acetate; 40 mM tris; 2 mM EDTA; pH 8.3.

TB-1 Buffer:

100 mM NaCl; 2 mM KCl; 1 mM $CaCl_2$; 1 mM $MgCl_2$; 10 mM HEPES; pH 7.5.

TE Buffer (10×):

0.1 M tris-HCl; 0.01 M EDTA, pH 8.0.

TED Buffer:

10 mM tris-HCl pH 7.6; 1 mM EDTA; 1 mM DTT.

1.6: Methods.

1.6.1: Growing.

Aerobic Cultivation.

Growing *E. coli* was performed in 100 ml conical flasks at 37° C. and 160 rpm on a rotary shaker in LB medium. For the selection of plasmid-carrying strains, the antibiotic ampicillin (50 µg/ml) was used. Precultures of the yeast *S. cerevisiae* were prepared at 30° C. and 160 rpm in 100 ml conical flasks and main cultures were prepared in 250 ml baffled flasks on a rotary shaker. If not explicitly described otherwise, all cultivations of the yeast *S. cerevisiae* were performed in WMVIII medium (C. Lang, A. C. Looman. Appl. Microbiol. Biotechnol. (1995) 44: 147-156), supplemented with 1 mg/ml histidine.

Anaerobic Cultivation.

If explicitly noted, the cultivation of the strain *S. cerevisiae* GRFura3 pFlat3-rSERT or pFlat3-leer was made under strictly anaerobic conditions, as follows: A 20 ml preculture was prepared, as mentioned under "Aerobic cultivation", for 48 h. The main culture was inoculated with 1% with this preculture and cultivated in a 250 ml baffled flask in 50 ml WMVIII medium, supplemented with 1 mg/l histidine and 40 mg/l cholesterol, under strictly anaerobic conditions at 30° C. and 160 rpm on a rotary shaker. For this purpose, the baffled flask was incubated in a 2.5 l anaerobic jar (Merck, Darmstadt) together with two gas packs (Anaerocult A, Merck, Darmstadt). The cholesterol supplementation was made with 0.5 ml (pro 50 ml medium) of a cholesterol solution (2.5 g ethanol; 2.5 g Tween 80; 20 mg cholesterol), so that a final concentration of 40 mg cholesterol per 1 liter medium resulted.

1.6.2: Methods of the DNA Analysis

Restriction

The restriction of the DNA (1 to 10 µg) was made in 30 µl batches, consisting of DNA, 3 µl of the corresponding buffer, 1 µl RSA (3 mg/ml) and 1 U enzymes (NotI and XhoI, BioLabs, Schwalbach) per 1 µg used DNA. The batch was incubated at 37° C. for two hours. For the restriction of PCR amplificates, an incubation for four hours was made.

Agarose Gel Electrophoresis

The agarose gel electrophoresis was made in mini-gel apparatuses (BioRad, Munich). The gels consisted of 1% agarose in TAE buffer. As electrophoresis buffer, TAE buffer was again used. 10 µl of the sample were reacted with 3 µl of a stopper solution. For fragments between 2 kb and 13 kb, λ-DNA (BioLabs, Schwalbach) restricted with HindIII (band size: 23.1 kb; 9.4 kb; 6.6 kb; 4.4 kb; 2.3 kb; 2.0 kb and 0.6 kb) served as standard. For smaller fragments between 500 bp and 3 kb, the marker GeneRuler (MBI Fermentas, St. Leon-Rot) was used, and for fragments between 3 kb and 10 kb, the marker 1 kb DNA Ladder (New England Biolabs) was used. For the fractionation of DNA fragments, a voltage of 100 V was applied for 30-45 min. Then, the gel was dyed in an ethidium bromide solution (0.4 mg/l TAE buffer) and received under UV light (254 nm).

DNA Precipitation

DNA from aqueous solutions was concentrated by means of a precipitation. For this purpose, the DNA solution was reacted with 1/10 volume 3 M sodium acetate (pH 4.8) and a 2.5 times larger volume ethanol (96%). The batch was incubated for 30 min at −20° C. and then centrifuged at 14,000 g. The DNA pellet was then again washed with 70% ethanol and centrifuged at 14,000 g for 5 min. The air-dried pellet was resuspended in a desired volume of TE buffer and stored at −20° C.

Ligation

The T4-DNA ligase catalyzes the linking of covalent phosphodiester bonds between the 3'-hydroxyl group of a nucleotide and the 5'-phosphate group of a second nucleotide in a double-strand DNA. The fragments to be ligated were purified by means of a DNA purification kit (Qiagen, Hilden) following the manufacturer's instructions and unified in a vector to insert DNA proportion of 3:1 and received in a volume of 17 µl. Thereafter, 2 µl ligase buffer (MBI Fermentas, St. Leon-Rot) and 1 µl T4 ligase (1 U/µl) were added and the batch was incubated for 2 hours in the case of a "sticky end ligation" at 16° C.

Competent Cells and Transformation of E. coli

The transformation of E. coli cells with plasmid DNA was made using the electroporation method. For preparing electrocompetent cells, an over-night culture was inoculated by 1% in 500 ml fresh LB medium and aerobically grown at 37° C. up to an optical density of 0.5-0.7. Then, the cells were centrifuged at 5,000 g for 10 min and resuspended in 200 ml ice-cold 10% glycerol. After another centrifugation step at 5,000 g for 10 min, the cells were resuspended in 100 ml ice-cold 10% glycerol. After another centrifugation at 5,000 g for 10 min and resuspension in 50 ml ice-cold 10% glycerol, the cells were centrifuged for 10 min at 5,000 g, the supernatant was removed and the pellet was resuspended in the flowing-back glycerol, split up in 65 µl aliquots and frozen at −80° C. For transformation, 100-200 ng plasmid DNA were mixed with 30 µl of the competent cells in an 1.5 ml Eppendorf vessel and incubated for one minute on ice. Then, the batch was transferred into sterile electroporation cuvettes pre-cooled on ice, and the electroporation (1.67 kV, 25 µF, 200Ω, 5 ms) was performed with a Multiporator (Eppendorf, Hamburg). After pulse application, the immediate addition of 1 ml YE medium and the transfer into a 1.5 ml Eppendorf vessel took place. The batch was now incubated for regeneration for 1 h at 37° C. and then plated-out on LB-agar plates with ampicillin for selection.

Isolation of Plasmid DNA from E. coli (Miniprep)

The respective E. coli strains were inoculated in 5 ml LB medium with 50 mg/l ampicillin and grown over night at 37° C. The cells were then centrifuged at 5,000 g. The supernatant was removed and the plasmid DNA was processed by means of a Miniprep kit (Qiagen, Hilden) following manufacturer's instructions.

Polymerase Chain Reaction (PCR)

By the polymerase chain reaction, it is possible to amplify DNA fragments by means of specific primers from isolated DNA or directly from whole E. coli cells. As a standard for a PCR reaction, 100 ng template DNA, dissolved in 1 µl $H_2O$ or an E. coli colony, transferred with a tooth picker into a PCR tube (colony PCR), were used. Besides the template, there was a reaction batch of 4 µl dNTP mix (2.5 mM), 5 µl 10× reaction buffer, 2 µl each primer (forward and reverse), 0.2 µl (1 U) Taq polymerase (Promega, Mannheim) or Takara polymerase (Takara, Tokyo, Japan) and $H_2O$ in a total volume of 50 µl. The PCR was carried out in a Thermocycler (Biorad, Munich) according to batch. For analysis, 10 µl of the PCR batches were resolved on an agarose gel or purified for further use by means of a PCR purification kit (Qiagen, Hilden) and concentrated to a volume of 30 µl.

Yeast Transformation

For the yeast transformation, a preculture in 20 ml YE medium was cultivated over night. A 50 ml main culture was inoculated to an optical density $OD_{600}$ of 0.3 and cultivated for approx. 4 hours. When an $OD_{600}$ of 0.8-1.0 was obtained, the cells were centrifuged at 4,000 g for 10 min, and the cells pellet was washed with 10 ml sterile $H_2O$. Thereafter, the cells were received in 1.5 ml $H_2O$ and transferred into an Eppendorf vessel. The cells were centrifuged (4,000 g, 2 mM) and resuspended in 1 ml lithium acetate solution (100 mM LiAc in TE buffer), centrifuged (4,000 g, 2 min) and again washed with 1 ml lithium acetate solution. Then, the cells were received in 200 µl lithium acetate solution (competent cells). For a transformation batch, 40 µl competent cells, 10 µl herring sperm DNA (10 mg/ml), 230 µl PEG solution (40% PEG 4000 in 0.1 M lithium acetate in 1× TE pH 8.0) and 1-20 µg DNA to be transformed were used. This batch was incubated for 30 min at 30° C. and thereafter exposed for 8 min to a heat shock at 42° C. After cooling to ambient temperature, 800 µl $H_2O$ were added and the batch was centrifuged at 7,000 g for 20 s. Then, the cells were directly plated out on corresponding selection media with agar and incubated for 3 to 5 days at 30° C. In the case of the double transformation mentioned in Chapter 4.2.2, i.e. the simultaneous transformation with 2 vectors, the transformation batch contained approx. 30 µg of each vector. For this, the vector DNA was precipitated and received in 10 µl $H_2O$. 40 µl competent cells were added and this batch was incubated for 30 min at 37° C., before the PEG solution and the herring sperm DNA were added. Thereafter as described above.

1.6.3: Sterol Analysis

Cultivation Conditions for the Sterol Analysis

For the sterol analysis, yeast cultures were carried out according to the following scheme: A 20 ml preculture was inoculated with 50 µl of a frozen culture and cultivated for 2 days. The main culture was carried out in 250 ml baffled flasks with 50 ml medium (WMVII medium, supplemented with 1 mg/ml histidine) on a rotary shaker at 160 rpm and 30° C. for 1 or 3 days, respectively. The main culture was inoculated with 1% of the preculture.

Determination of the Dry Substance

For the determination of the dry substance, 3 times 6 ml culture volume were transferred into 15 ml Greiner tubes previously weighed out. The cells were centrifuged at 3,500 g for 5 min and washed with 10 ml H$_2$O. Then, the cells pellet was dried in a heating oven for 12 hours at 80° C. The samples cooled down in the exsiccator, before weighing was carried out.

Processing of the Total Sterols

The cells to be investigated were harvested and washed with 40 ml H$_2$O. Then, the optical density OD$_{600}$ was determined and a yeast pellet, corresponding to 125 OD$_{600}$ was received in 5 ml 0.5 N HCl solution. The suspension was then boiled in a 50 ml Falcon tube for 20 min at 100° C. The thus labilized cells were thereafter cooled down on ice and 3 g KOH were added to the solution. After dissolving of the KOH, 12.5 ml of a 0.25 g/l methanolic pyrogallol solution were added. As an extraction standard, 10 µl cholesterol solution (10 mg/ml) were additionally added. The saponification mixture was incubated for 1 h 45 min at 70° C. After cooling down of this batch to ambient temperature, the sterols were extracted with 2×20 ml n-hexane. The combined n-hexane phases were concentrated at the rotary evaporator and the residue was dissolved with 2×1 ml chloroform with 0.2 g/l nonadecane as an internal standard and transferred into brown glass bottles. The sterol extracts were stored at −20° C. before analysis.

Processing of the Membrane Sterols

For the preparation of the samples for the membrane sterol analysis, first the plasma membranes of the strains of the yeast S. cerevisiae to be investigated had to be isolated. This was made according to the method of Serrano (Serrano et al., Methods Enzymol., 157:533-544 (1988)) with a few modifications, which will be described in brief in the following: The cells were received after the harvest and a washing step with H$_2$O in 1 ml 1M tris (pH 8), 200 µl 0.5 M EDTA and 100 µl 200 mM PMSF. Then occurred the disruption using glass beads. After a centrifugation step, the supernatant was removed, the glass beads were washed with TED buffer and the supernatants were unified in a SS34 tube. Larger membrane vesicles and the plasma membrane were now pelletized at 20,000 g for 30 min and the pellet was received in 4 ml 20% glycerol in TED buffer with 200 µl 0.2 M PMSF and homogenized with a Dounce homogenizer. 3 ml of this homogenate were given on a discontinuous gradient, of 6 ml 53% (w/w) and 3 ml 43% (w/w) saccharose in a Beckman Ultracentrifuge tube. Centrifugation occurred for 6 h at 100,000 g in a Beckman SW41-Ti rotor. The purified plasma membrane could be removed with a Pasteur pipette from the interphase and was transferred into a new Beckman tube, which was filled up with H$_2$O. The plasma membrane was thereafter pelletized at 80,000 g for 30 min and the pellet was resuspended in 2 ml TED buffer and stored at −20° C. For the extraction of the sterols, 1 ml of the plasma membrane suspension was reacted with 500 µl chloroform and vortexed for 1 min. Then followed the phase separation at 13,000 rpm for 15 min. 450 µl of the lower organic phase were now transferred into a GC tube and 50 µl N-methyl-N-trimethylsilyltrifluoroacetamide (MSTFA, Sigma, Munich) were added. The derivatization of the sterols was performed for 1 h at 80° C. The ready samples could now be analyzed by gas chromatography.

Conditions for the Gas Chromatography (GC)

The GC analysis was carried out with an Agilent 6890N gas chromatograph (Agilent, Waldbronn), equipped with an Autosampler Agilent 7683B. As a detector, an Agilent 5975 VL mass spectrometer was used. The following conditions were selected: The column was a 30 m long HP-5MS column (J&W Scientific, USA) with an inner diameter of 0.25 mm and a film thickness of 0.25 µm. Helium served as mobile phase. The GC/MS system was operated with a temperature program (100° C. 0.5 min, 50° C./min to 270° C., 270° C. for 10 min, 5° C./min to 290° C., 290° C. for 4 min, 5° C./min to 325° C., 325° C. for 20 min, 5° C./min to 340° C., 340° C. for 2 min) in the splitless mode. The injector temperature was 280° C., that of the detector was 150° C. For a better separation and the increase of the volatility of sterol intermediates, the sterol sample were derivatized with MSTFA for one hour at 80° C. in the heating oven. The determination of the molar masses of the investigated sterol intermediates, and the identification thereof by means of the ionization pattern, was carried out with the Agilent 5975 VL mass spectrometer. The injection volume of the samples was 2 µl.

Example 2: Results

In the year 2002, the biosynthesis of cholesta-5,7,24-trien-3-ol in the yeast S. cerevisiae could be established (Veen, 2002, see above). For this purpose, a freely obtainable lab strain GRF18 as shown in the following was modified with genetic methods.

| Strain | | Description |
| --- | --- | --- |
| GRF18 | ↓ | leu2, his3 |
| GRFura3 | ↓ | leu2, his3, ura3 |
| GRFtH3 | ↓ | tHMG1-leu2, his3, ura3 |
| GRFtH3E1e5 | ↓ | tHMG1-leu2, ERG1-erg5, his3, ura3 |
| GRFtH1E1E11e5e6 | | tHMG1-leu2, ERG1-erg5, ERG11-erg6, his3, ura3 |

As can be seen, first the gene URA3 was deleted and the gene tHMG1 was integrated at the gene locus LEU2. The gene tHMG1 (t=truncated, cut short) codes for a cut short HMG-CoA reductase, which only consists of the catalytic subunit of the protein and is thus not subject anymore to the feedback inhibition by sterol intermediates. The transcription of the gene tHMG1 is controlled by the constitutive ADH1 promoter. By the analysis of a systematic overexpression and transcriptional deregulation of all genes of the post-squalene biosynthesis pathway individually and in combinations in the HMG1-deregulated strain, two further main regulation points or bottlenecks in the post-squalene pathway could be identified. These bottlenecks could be overcome by the overexpression of the squalene epoxidase (ERG1) and the lanosterol demethylase (ERG11). For this purpose, the genes ERG1 and ERG11 were integrated in the yeast genome in a transcriptionally deregulated form under the control of a constitutive ADH1 promoter, and that by means of homologous recombination at the loci of the genes ERG5 and ERG6, which thereby were deleted (Veen, 2002, see above). Thus, in 3 transformation steps only, 5 genetic modifications were introduced into the yeast strain, by which a removal of the bottlenecks in the ergosterol synthesis pathway, and the establishment of the synthesis of cholesta-5,7,24-trien-3-ol is achieved. In addition, it was found that the resulting yeast strain GRFtH1E1E11e5e6 (GRFco1) produces post-squalene sterol intermediates in far bigger quantities than the wild type strain GRFura3.

In another step, according to the invention, a dehydrocholesterol-delta7 reductase (known from the document U.S.

Pat. No. 5,759,801) was brought to overexpression in this strain by means of the shuttle vector pFlat1.

For this purpose, the cDNA for the dehydrocholesterol-delta7 reductase (DHCR7) from *Arabidopsis thaliana* was integrated between the constitutive ADH1 promoter and the tryptophan terminator (TRP1) of the vector and transformed into the yeast. The resulting yeast strain was designated GRFco1 pFlat1-DHCR7.

Figure 1:
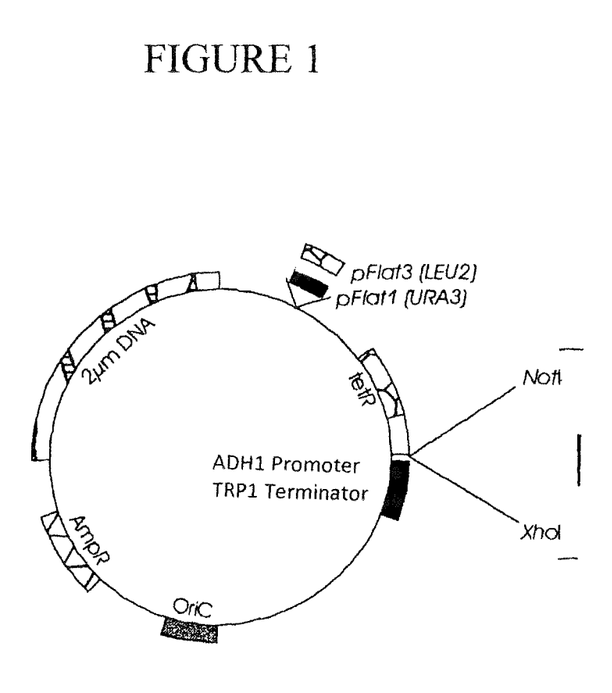
FIG. 1 shows a diagrammatic representation of the episomal yeast expression plasmids pFlat1 and pFlat3.

The gas-chromatographic analysis of the total sterol composition is explained in the following. Table 2 shows the composition of the main sterols in the yeast GRFco1 after transformation with the vector pFLAT1-DHCR7, which contains the dehydrocholesterol-$\Delta 7$ reductase from *Arabidopsis thaliana*, and/or pFlat3-DHCR24, which contains the dehydrocholesterol-$\Delta 24$ reductase from *Xenopus laevis*. The values originate from a GC/MS analysis and are percentage shares. It can be seen that the overexpression of the DHCR7 led to a partial conversion of the cholesta-5,7,24-trienol into cholesta-5,24-dienol (desmosterol), a direct cholesterol prestage. The share of this sterol in the total sterol content of the yeast was approx. 40-50%. Thus, desmosterol was the main sterol in the yeast, besides zymosterol. The investigation of the plasma membrane resulted in that desmosterol with a share of approx. 60% was the main membrane sterol (data not shown).

gene and pFlat3 carries a LEU2 gene for the selection of plasmid-carrying strains. Both plasmids contain the constitutive ADH1 promoter and the TRP1 terminator, as well as the largest part of the 2 μm DNA for the replication. The cloning of the rSERT cDNA between the restriction sites NotI and XhoI of the multiple cloning site is diagrammatically shown.

After establishment of the vector pFlat3 rSERT, the strain GRFco1 pFlat1-DHCR7 as well as the wild type strain GRF 18 were transformed with the plasmid, and the serotonin receptor was brought to expression. The functional expression of the rSERT in the yeast strains to be investigated was verified by binding [$^3$H] citalopram to spheroblasts. Serotonin antagonists, such as citalopram, exclusively bind to correctly folded and active, i.e. to functionally expressed SERT molecules. Citalopram binds with high affinity to the same site of the serotonin transporter as the actual substrate, serotonin. An indication for this is that citalopram reduces the maximum number of the binding sites, does however not lower the affinity of the serotonin for the SERT. It is known that [$^3$H] citalopram only binds to the rSERT, if cholesterol is present in the surrounding membrane. Ergosterol could not replace cholesterol in this study. Whether this is possible with the sterols cholesta-5,7,24-trienol and desmosterol,

TABLE 2

Percentage share of the respective sterol in the mentioned strains (total sterols).

| Strain | Cholesterol | Demosterol | Zymosterol | Cholesta-7,24-dienol | Ergosterol | Cholesta-5,7,24-trienol | Squalene | 7-Dehydro-cholesterol |
|---|---|---|---|---|---|---|---|---|
| GRFco1 pFlat1 pFlat3 | 0.0 | 0.0 | 14.5 | 14.0 | 5.3 | 25.4 | 40.7 | 0.0 |
| GRFco1 pFlat1 DHCR7 pFlat3 | 0.0 | 47.3 | 8.7 | 5.5 | 4.2 | 13.1 | 21.3 | 0.0 |
| GRFco1 pFlat1-DHCR7 pFlat3-DHCR24 *X. laevis* | 3.2 | 41.7 | 6.6 | 4.8 | 5.7 | 8.9 | 22.1 | 7.0 |

After the establishment of the demosterol biosynthesis, by means of the shuttle vector pFlat3, a dehydrocholesterol-$\Delta 24$ reductase was expressed in the yeast additionally to DHCR7. For this purpose, the cDNA for the dehydrocholesterol-$\Delta 24$ reductase (DHCR24) from *Xenupus laevis* was integrated between the constitutive ADH1 promoter and the tryptophan terminator (TRP1) of the pFlat3 vector and introduced into the yeast. The resulting strain was designated GRFco1 pFlat1-DHCR7 pFlat3-DHCR24. The gas-chromatographic analysis of the total sterol composition of this strain showed that the overexpression of the DHCR24 led to the synthesis of cholesterol and 7-dehydrocholesterol. The share of cholesterol and 7-dehydrocholesterol was approx. 3.2 and 7.0%, respectively (Table 1).

For verifying the influence of desmosterol on the heterologous expression of a membrane protein, the serotonin transporter of the rat was overexpressed in the strain GRFco1 pFlat1-DHCR7. For this purpose, the rSERT-cDNA was integrated between the constitutive ADH1 promoter (C. Lang, A. C. Looman, Appl. Microbiol. Biotechnol. 44: 147-156 (1995)) and the tryptophan terminator (TRP1) of the pFlat3 vector. The integration occurs by a NotI and a XhoI restriction site in the "multiple cloning site" of this *E. coli/S. cerevisiae* "shuttle vector". The pFlat vector system is diagrammatically shown in FIG. 1. It shows a diagrammatic representation of the episomal yeast expression plasmids pFlat1 and pFlat3. The plasmid pFlat1 carries a URA3 which are more similar to the structure of cholesterol, should be investigated in an experiment.

Figure 2:
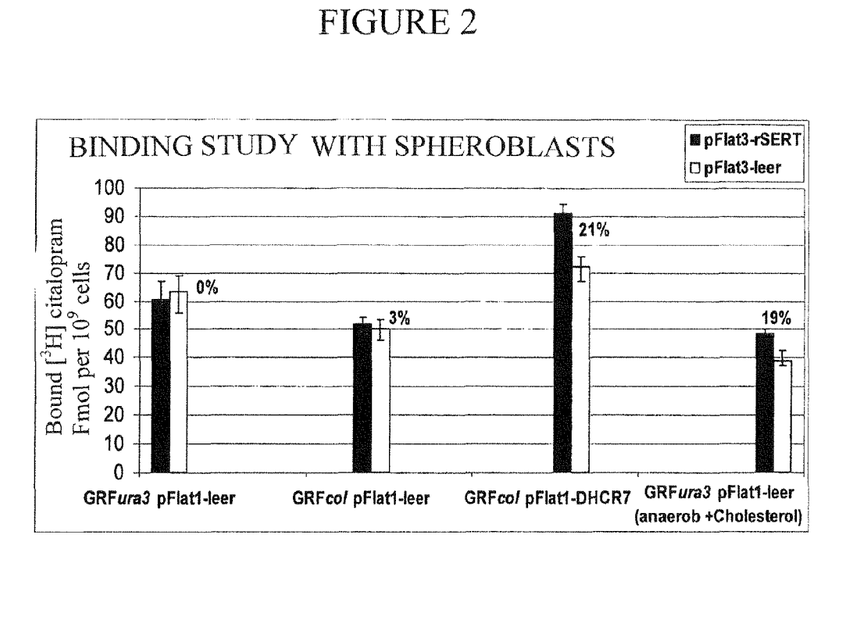
FIG. 2 shows a scintillation count of bound [$^3$H] citalopram in fmol per 109 cells. The results of the binding study shows that the non-specific binding is highest for GRFco1-DHCR7 and lowest for GRFura3 anaerobic+cholesterol.

In order to verify the functional expression of the rSERT in the plasma membrane of the yeast strains to be investigated, a [$^3$H] citalopram binding study with spheroblasts of these strains was carried out. FIG. 2 shows the results of this study. Shown is a scintillation count of the bound [$^3$H] citalopram in fmol per $10^9$ cells. Spheroblasts of the strains GRFura3 pFlat1-leer, pFlat3-rSERT; GRFco1 pFlat-leer, pFlat3-rSERT; GRFco1 pFlat1-DHCR7, pFlat3-rSERT; GRFura3 pFlat1-leer, pFlat3-rSERT anaerobically cultivated with cholesterol supplementation and the corresponding control strains (in order to determine the non-specific binding, carry the pFlat3-leer vector) were incubated with 2 nM [$^3$H] citalopram. The indicated per-centages represent the specific binding relative to the total binding. The height of bars represents the mean value from three independent experiments. The error bars indicate the largest and the smallest measurement values.

FIG. 2 shows that the non-specific binding is highest for GRFco1-DHCR7 and lowest for GRFura3 anaerobic+cholesterol.

A significant difference between specific and non-specific binding to spheroblasts of GRFura3 and GRFco1, and thus a functional expression of the rSERT in these strains, cannot be taken from the results in FIG. 2. It is however surprising that besides GRFura3 anaerobic with cholesterol, a specific binding of the [³H] citalopram of approx. 20% can also be detected for GRFco1-DHCR7. This corresponds to a specific binding of on average 6 molecules [³H] citalopram or the functional expression of 6 molecules rSERT per cell of the strain GRFura3 anaerobic with cholesterol. In the case of GRFco1-DHCR7, it corresponds to 11 molecules. The difference of 5 molecules can be explained by the different expression level of the SERT in the two strains. An analysis of the expression levels per Western blot (data not shown) showed that the expression in GRFco1-DHCR7 is larger than in GRFura3 anaerobic with cholesterol.

The specific binding is approx. 20% in GRFura3 anaerobic with cholesterol as well as in GRFco1-DHCR7. That means, desmosterol obviously fully compensates the lack of cholesterol, with regard to the functionality of the SERT. The results of the binding study with spheroblasts indicate a functional expression of the rSERT in GRFco1-DHCR7.

For spheroblasts of the strain GRFura3 pFlat3-rSERT anaerobic with cholesterol, a specific binding of [³H] citalopram could be detected. Thus, it can be assumed that the rSERT in this strain is functionally expressed under these cultivation conditions. Since spheroblasts were involved, the proof of the expression of the rSERT in the plasma membrane was also accomplished. The results in FIG. 2 illustrate that ergosterol and cholesta-5,7,24-trienol cannot compensate the lack of cholesterol, and that cholesterol or desmosterol in the membrane is necessary for a functional expression of the SERT.

What is claimed is:

1. An isolated genetically modified living non-mammal yeast organism, having an increased HMG-CoA reductase activity compared to the wild type, and having a reduced C24 methyltransferase and/or delta22 desaturase activity compared to the wild type, wherein the organism has an increased dehydrochole-sterol-delta7 reductase activity compared to the wild type and is additionally transformed with a gene coding for a membrane protein of a mammal.

2. The organism of claim 1, wherein the organism additionally has an increased dehydrocholesterol-delta24 reductase activity compared to the wild type.

3. The organism of claim 1, wherein the organism has an increased squalene epoxidase and/or lanosterol demethylase activity compared to the wild type.

4. The organism of claim 1, wherein the yeast is selected from the group consisting of *Saccharomyces cerevisiae, Saccharomyces delbruckii, Saccharomyces italicus, Saccharomyces ellipsoideus, Saccharomyces fermen-tati, Saccharomyces kluyveri, Saccharomyces kru-sei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces ovarium* and *Saccharomyces ludwigii*, as well as yeasts of the species *Kluyveromyces* such as *K. lactis K. marxianus* var. *marxianus, K. thermotolerans*, and yeasts of the species *Candida* such as *Candida utilis, Candida tropicalis, Candida albicans, Candida lipolytica* and *Candida versatilis*, and yeasts of the species *Pichia* such as *Pichia stipidis, Pichia pastoris* and *Pichia sorbitophila*, and yeasts of the species *Cryptococcus, Debaromyces, Hansenula, Saccharomycecopsis, Saccharomyces, Schizosaccharomyces, Wickerhamia, Debayomyces, Hanseniaspora, Kloeckera, Zygosaccharomyces, Ogataea, Kuraishia, Komagataella, Metschnikowia, Williopsis, Nakazawaea, Cryptococcus, Torulaspora, Bullera, Rhodotorula, Willopsis* and *Sporobolomyces*.

5. The organism of claim 1, comprising, preferably a membrane, most preferably a plasma membrane, with an increased content of desmosterol and/or cholesterol and/or 7-dehydro-cholesterol and/or lathosterol compared to the wild type.

6. The organism of claim 1, wherein the organism is transformed with a human membrane protein, preferably a plasma membrane protein, under the control of a preferably constitutively active promoter.

7. A kit comprising an organism of claim 1, optionally with a nucleic acid construct suitable for the transformation of the organism and containing a nucleic acid coding for a membrane protein of a mammal, preferably a human membrane protein, most preferably a plasma membrane protein, which is under the control of a preferably constitutively active promoter, and comprising instructions of use for transforming the organism with the nucleic acid construct, cultivating the organism before and after the transformation, contacting the organism with a given substance or a given mixture of substances, and measuring a modification of a property of the organism and/or a binding of the substance or mixture of substances to the membrane protein.

* * * * *

SEQUENCE LISTING

```
<160> NUMBER OF SEQ ID NOS: 3

<210> SEQ ID NO 1
<211> LENGTH: 31
<212> TYPE: DNA
<213> ORGANISM: Artificial
<220> FEATURE:
<223> OTHER INFORMATION: synthesized

<400> SEQUENCE: 1
atgcggccgc accatggaga ccacaccttt g                              31

<210> SEQ ID NO 2
<211> LENGTH: 27
<212> TYPE: DNA
<213> ORGANISM: Artificial
<220> FEATURE:
<223> OTHER INFORMATION: synthesized

<400> SEQUENCE: 2
atctcgagtt acacagcatt catgcgg                                   27

<210> SEQ ID NO 3
<211> LENGTH: 1578
<212> TYPE: DNA
<213> ORGANISM: Artificial
<220> FEATURE:
<223> OTHER INFORMATION: synthesized

<400> SEQUENCE: 3
atggaccaat tggtgaaaac tgaagtcacc aagaagtctt ttactgctcc tgtacaaaag    60
gcttctacac cagtttaac caataaaaca gtcatttctg gatcgaaagt caaaagttta   120
tcatctgcgc aatcgagctc atcaggacct tcatcatcta gtgaggaaga tgattcccgc   180
gatattgaaa gcttggataa gaaatacgt cctttagaag aattagaagc attattaagt   240
agtggaaata caaaacaatt gaagaacaaa gaggtcgctg ccttggttat tcacggtaag   300
ttacctttgt acgctttgga gaaaaaatta ggtgatacta cgagagcggt tgcggtacgt   360
aggaaggctc tttcaatttt ggcagaagct cctgtattag catctgatcg tttaccatat   420
aaaaattatg actacgaccg cgtatttggc gcttgttgtg aaaatgttat aggttacatg   480
cctttgcccg ttggtgttat aggcccctg gttatcgatg gtacatctta tcatatacca   540
atggcaacta cagagggttg tttggtagct tctgccatgc gtggctgtaa ggcaatcaat   600
gctggcggtg gtgcaacaac tgtttaact aaggatggta tgacaagagg cccagtagtc   660 cgttccaa ctttgaaaag atctggtgcc tgtaagatat ggtagactc agaagaggga   720 caaaacgcaa ttaaaaagc ttttaactct acatcaagat ttgcacgtct gcaacatatt   780
```

-continued

```
caaacttgtc tagcaggaga tttactcttc atgagattta gaacaactac tggtgacgca    840
atgggtatga atatgatttc taaaggtgtc gaatactcat taaagcaaat ggtagaagag    900
tatggctggg aagatatgga ggttgtctcc gtttctggta actactgtac cgacaaaaaa    960
ccagctgcca tcaactggat cgaaggtcgt ggtaagagtg tcgtcgcaga agctactatt   1020
cctggtgatg ttgtcagaaa agtgttaaaa agtgatgttt ccgcattggt tgagttgaac   1080
attgctaaga atttggttgg atctgcaatg gctgggtctg ttggtggatt taacgcacat   1140
gcagctaatt tagtgacagc tgttttcttg gcattaggac aagatcctgc acaaaatgtt   1200
gaaagttcca actgtataac attgatgaaa gaagtggacg gtgatttgag aatttccgta   1260
tccatgccat ccatcgaagt aggtaccatc ggtggtggta ctgttctaga accacaaggt   1320
gccatgttgg acttattagg tgtaagaggc ccgcatgcta ccgctcctgg taccaacgca   1380
cgtcaattag caagaatagt tgcctgtgcc gtcttggcag gtgaattatc cttatgtgct   1440
gccctagcag ccggccattt ggttcaaagt catatgaccc acaacaggaa acctgctgaa   1500
ccaacaaaac ctaacaattt ggacgccact gatataaatc gtttgaaaga tgggtccgtc   1560
acctgcatta aatcctaa                                                 1578
```

UNITED STATES PATENT AND TRADEMARK OFFICE
CERTIFICATE OF CORRECTION

Page 1 of 1

PATENT NO. : 9,920,348 B2
APPLICATION NO. : 14/458639
DATED : March 20, 2018
INVENTOR(S) : Schilling et al.

It is certified that error appears in the above-identified patent and that said Letters Patent is hereby corrected as shown below:

On the Title Page

Insert:
Item --(30) Foreign Application Priority Data
May 21, 2009   (DE) ...................... 102009022772.5--

Signed and Sealed this
Thirtieth Day of October, 2018

Andrei Iancu
*Director of the United States Patent and Trademark Office*